United States Patent
Lee

(10) Patent No.: US 9,456,963 B2
(45) Date of Patent: Oct. 4, 2016

(54) PHOTO-CURABLE RESIN COMPOSITIONS AND METHOD OF USING THE SAME IN THREE-DIMENSIONAL PRINTING FOR MANUFACTURING ARTIFICIAL TEETH AND DENTURE BASE

(71) Applicant: DENTCA, Inc., Los Angeles, CA (US)

(72) Inventor: Jae Sik Lee, Los Angeles, CA (US)

(73) Assignee: Dentca, Inc., Torrance, CA (US)

( * ) Notice: Subject to any disclaimer, the term of this patent is extended or adjusted under 35 U.S.C. 154(b) by 465 days.

(21) Appl. No.: 13/865,907

(22) Filed: Apr. 18, 2013

(65) Prior Publication Data

US 2014/0167300 A1 Jun. 19, 2014

Related U.S. Application Data

(60) Provisional application No. 61/738,970, filed on Dec. 18, 2012.

(51) Int. Cl.
| | | |
|---|---|---|
| C08F 2/46 | (2006.01) | |
| C08F 2/50 | (2006.01) | |
| C08G 61/04 | (2006.01) | |
| A61K 6/083 | (2006.01) | |
| A61C 13/00 | (2006.01) | |

(52) U.S. Cl.
CPC ........... *A61K 6/083* (2013.01); *A61C 13/0013* (2013.01)

(58) Field of Classification Search
CPC ...... A61K 6/083; B33Y 70/00; A61C 13/20; A61C 13/0013; B29C 67/0055
USPC .............................. 522/96, 90, 1, 113; 520/1
See application file for complete search history.

(56) References Cited

U.S. PATENT DOCUMENTS

| 6,821,462 B2 | 11/2004 | Schulman et al. |
| 2002/0033548 A1 | 3/2002 | Brodkin et al. |
| 2007/0049656 A1* | 3/2007 | Jia et al. ........................ 523/116 |
| 2008/0287564 A1 | 11/2008 | Klare et al. |
| 2010/0016464 A1* | 1/2010 | Craig et al. ................... 523/115 |
| 2011/0049738 A1 | 3/2011 | Sun et al. |
| 2011/0275035 A1 | 11/2011 | Lu |
| 2012/0093741 A1 | 4/2012 | Maletz et al. |
| 2012/0196249 A1* | 8/2012 | Maletz et al. ................ 433/173 |
| 2014/0239527 A1* | 8/2014 | Lee ................................ 264/17 |

OTHER PUBLICATIONS

Froes-Salgado et al, Influence of the Base and Diluent Methacrylate Monomers on the Polymerization Stress and Its Determinants, Sep. 1, 2011, Journal of Applied Polymer Science, vol. 123, 2985-2991.*
PCT International Application No. PCT/US2013/037218, Notification of Transmittal of the International Search Report and the Written Opinion of the International Searching Authority, or Declaration dated Sep. 4, 2013, 14 pages.
PCT International Application No. PCT/US2014/036975, Written Opinion of the International Searching Authority dated Sep. 5, 2014, 13 pages.

* cited by examiner

*Primary Examiner* — Ling Choi
*Assistant Examiner* — Jessica E Whiteley
(74) *Attorney, Agent, or Firm* — Lee, Hong, Degerman, Kang & Waimey; Jonathan Y. Kang; Harry S. Lee

(57) ABSTRACT

Photo-curable compositions for artificial teeth and denture base and a method for manufacturing denture by a three-dimensional printing system are provided. The compositions include photo-curable organic compounds, surface modified nano-sized inorganic filler, photo-initiator, colorant, and stabilizer. The composition is in a viscous liquid state having 1500-5000 cps at ambient temperature and has a low viscosity of 50-500 cps at jetting temperature or dispensing temperature. The composition also has an excellent curing rate for three-dimensional printing. Using the compositions, denture having a distinctive denture base and a set of artificial teeth can be manufactured via an inkjet type or digital light process type three-dimensional printing according to Computer Aided Design (CAD) data.

14 Claims, 3 Drawing Sheets

PHOTO-CURABLE RESIN COMPOSITIONS AND METHOD OF USING THE SAME IN THREE-DIMENSIONAL PRINTING FOR MANUFACTURING ARTIFICIAL TEETH AND DENTURE BASE

CROSS REFERENCE TO RELATED APPLICATIONS

Pursuant to 35 U.S.C. §119(e), this application claims the benefit of Provisional Application No. 61/738,970 filed on Dec. 18, 2012, the contents of which are hereby incorporated by reference herein in their entirety.

FIELD OF INVENTION

The present invention relates to liquid type photo-curable resin compositions and a method for producing an artificial tooth or teeth and a denture base by a three dimensional printing process using the compositions. In particular, the present invention relates to dental compositions having low viscosity at a feeding temperature and a fast curing rate. Such compositions are used in three-dimensional printing to manufacture dentures having a distinctive denture base and a set of artificial teeth.

DESCRIPTION OF THE RELATED ART

In recent years, three-dimensional printing technologies have been used to produce a large number of items in a short period of time. There are several ways to build three-dimensional articles using photo-curable materials. One of the most efficient technologies for three-dimensional printing is an inkjet printing method of which the photo-curable material and support material are simultaneously jetted or only the photo-curable material is jetted through a single nozzle or a series of tiny nozzles onto a building plate and the applied material is then cured by ultraviolet/visible (UV/Vis) light. This method is also referred to as a layer-by-layer jetting method.

Another technology for three-dimensional printing is a digital light process method. In the digital light process method, the photo-curable material, which is in liquid form, is layered on a vat or spread on a sheet, and a predetermined area of the layered material is exposed to the UV/Vis light that is controlled by a digital micro-mirror device. In the digital light process method, additional layers are repeatedly or continuously laid and each layer is cured until a desired three-dimensional article is formed.

An inkjet printing system may be used to load and print several materials at once. The resolution of the inkjet printing system is controlled by a nozzle size and the material should have viscosity that is sufficiently low to pass through the nozzle and to allow rapid curing before a new layer is spread on top of the cured layer. In contrast, the resolution of the digital light process method generally depends on the viscosity of photo-curable materials and can be controlled by a thickness of layers formed. In addition, the digital light process method requires a support bar instead of a support material required in the inkjet printing method such that the number of loading materials is limited to only one material. For example, U.S. Pat. Nos. 7,183,335 and 7,300,619 disclose a composition for use in inkjet type three dimensional printing. According to the printing method disclosed in these patent documents, several materials can be loaded together and a high resolution may be achieved in minimum operation time. However, most compositions for inkjet type printing disclosed in these patent documents are comprised of acrylate type components which are not suitable for use in dentures.

Conventional dental compositions or mixtures react slowly and have high viscosity. For example, (meth)acrylate materials, such as methyl methacrylate, and high molecular weight poly methyl methacrylate have been used as materials for manufacturing artificial teeth and denture base resin because they are cheap and have good transparency, excellent moldability, and good physical properties. In general, the methyl methacrylate monomer has slower reactivity than an acrylate monomer and has characteristic odor while the high molecular weight polymethyl methacrylate has high viscosity and stickiness.

Moreover, inorganic fillers in micrometer size are used to provide good mechanical properties for artificial teeth and denture base. When methyl methacrylate monomer is mixed with polymethyl methacrylate and inorganic filler for making denture base or an artificial tooth, the mixture has dough-like characteristics or is very sticky and highly viscous such that the mixture is poured into the mold to form an artificial tooth or denture base. It takes a long time to cure such a mixture due to low reactivity of methyl methacrylate. Therefore, such conventional mixtures are not suitable for use in three-dimensional printing because of their slow reactivity, high viscosity, and high stickiness, as well as the inorganic fillers which are in micrometer size.

Since each patient has different mandibular arch and maxillary arch, each denture is manufactured uniquely on a case by case basis such that each denture is different from one another. Therefore, dentures are manufactured by professionally trained persons.

However, dentures manufactured manually by the professionals still tend to have some defects due to errors. In order to reduce errors in denture manufacture, there have been attempts to make artificial teeth and dentures using three-dimensional printing technologies.

For example, U.S. Pat. Nos. 5,496,682 and 7,927,538 disclose light-curable slips for stereolithographic preparation of dental ceramics. According to these patent documents, a flowable mixture, including sinterable inorganic particles, a photo-curable monomer, a photo-initiator and a dispersant, is spread over a substrate and cured in a selective pattern. Subsequent layers of the mixture are applied over the substrate and cured to build a three-dimensional body. Photo-curable materials used in systems disclosed in these patent documents play roles only as a binder to hold a certain form until the printed shape is solidified by a sintering process.

However, since a main component of the mixture is sinterable inorganic particles, a sintering process is required to remove organic binder. In addition, the method according to these patent documents provides only ceramic artificial teeth which may be easily broken by impact.

Further, U.S. Pat. No. 7,476,347 and U.S. Pat. Application Pub. No. 2011/0049738 disclose a process for making dentures having integral teeth and a denture base by inkjet type three-dimensional printing. In these patent documents, the cured specimen in a mold showed excellent mechanical properties.

However, in these patent documents, wax-like polymerizable materials were used in the printer, and since the wax-like polymerizable materials without filler are not readily available, they needed to be custom-synthesized, incurring additional time and costs. Moreover, according to some embodiments disclosed in these patent documents, materials mixed with more than 70% filler required 10 minutes to cure in a mold due to their slow reaction rate and high viscosity. Furthermore, there was difficulty in using the composition mixed with filler having different particle sizes for jetting in three-dimensional printing.

Thus, there is a need for simple and easily photo-curable compositions that are formulated to be suitable for construction of dentures using a three-dimensional printing method. There is a further need for simple and easily obtainable curable compositions for artificial teeth and denture base, which can be formulated to provide viscosity that is suitable for jetting through the jetting nozzle, viscosity that is suitable for dispensing through the slit on sheet or low viscosity in a vat and a fast-curing rate for three-dimensional printing by either an inkjet method or a digital light process method.

SUMMARY OF THE INVENTION

Photo-curable liquid compositions used for artificial teeth and denture base and a method for making dentures using the compositions and three-dimensional printing technology are provided. The inventive compositions for manufacturing denture base and artificial teeth have suitable viscosity and curing rate for three-dimensional printing, providing appropriate mechanical properties desired for denture base and artificial teeth. The inventive compositions also allow effective operation time for manufacturing dentures.

According to one exemplary embodiment of the present invention, an artificial tooth composition comprises about 50 to about 75 weight % of at least one kind of difunctional bisphenol A dimethacrylate, about 5 to about 15 weight % of at least one kind of multifunctional methacrylate having two or more methacryloxy groups, about 15 to about 35 weight % of at least one kind of urethane dimethacrylate, about 5 to about 35 weight % of at least one kind of a silica based fine particles having an average particle size of less than about 200 nm and having coated oxide layers or methacrylate functionalized layers, about 0.2 to about 5.0 weight % of at least one kind of a UV/Vis light-photo-polymerization initiator, at least one colorant, and at least one stabilizer.

According to another exemplary embodiment of the present invention, a denture base composition comprises about 40 to about 60 weight % of at least one kind of difunctional bisphenol A dimethacrylate, about 5 to about 20 weight % of at least one kind of multifunctional methacrylate, about 20 to about 45 weight % of at least one kind of urethane dimethacrylate, about 0 to about 15 weight % of at least one kind of a silica based fine particles having an average particle size of less than about 200 nm and having coated oxide layers or methacrylate functionalized layers, about 0.2 to about 5.0 weight % of at least one kind of a UV/Vis light-photo-polymerization initiator, at least one colorant, and at least one stabilizer.

DETAILED DESCRIPTION

Figure 1:
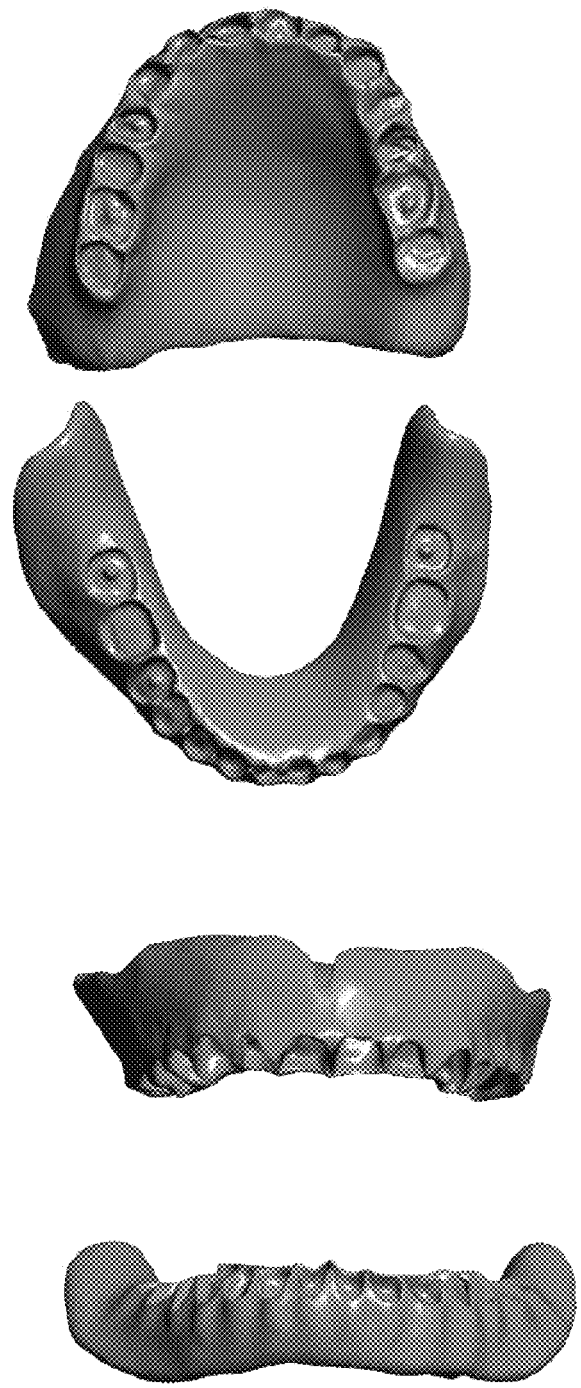
FIG. 1 is a schematic view of a denture base to be formed by three-dimensional printing and to be integrated with a set of artificial teeth according to an exemplary embodiment of the present invention.

The present invention relates to photo-curable compositions used to produce artificial teeth and denture base using a three-dimensional printing system. For example, a composition used for manufacturing an artificial tooth includes (a) about 50 to about 75 weight % of at least one kind of difunctional bisphenol A dimethacrylate, (b) about 5 to about 15 weight % of at least one kind of multifunctional methacrylate having two or more methacryloxy groups, (c) about 15 to about 35 weight % of at least one kind of urethane dimethacrylate, (d) about 5 to about 35 weight % of at least one kind of a silica based fine particles having an average particle size of less than about 200 nm and having coated oxide layers or methacrylate functionalized layers, (e) about 0.2 to about 5.0 weight % of at least one kind of a UV/Vis light-photo-polymerization initiator, (f) at least one colorant, and (g) at least one stabilizer.

The ratio of each component in the composition may be adjusted to obtain a desirable composition that is appropriate for manufacturing an artificial tooth. That is, for example, the ratio of the at least one kind of difunctional bisphenol A dimethacrylate in the composition may be anywhere between 50 and 75 weight % and amounts of the rest of the components will be adjusted according to the amount of the at least one kind of difunctional bisphenol A dimethacrylate used in the composition.

Further, an exemplary composition used for manufacturing a denture base includes (a) about 40 to 60 weight % of at least one kind of difunctional bisphenol A dimethacrylate, (b) about 5 to about 20 weight % of at least one kind of multifunctional methacrylate, (c) about 20 to about 45 weight % of at least one kind of urethane dimethacrylate, (d) about 0 to about 15 weight % of at least one kind of a silica based fine particles having an average particle size of less than about 200 nm and having coated oxide layers or methacrylate functionalized layers, (e) about 0.2 to about 5.0 weight % of at least one kind of a UV/Vis light-photo-polymerization initiator, (f) at least one colorant, and (g) at least one stabilizer. The ratio of each component in the composition may be adjusted to obtain a desirable composition that is appropriate for manufacturing a denture base.

As difunctional bisphenol A dimethacrylate, also known as monomeric bisphenol-A dimethacrylate having a bifunctionality, which provides excellent mechanical properties, high glass transition temperature, and a fast curing rate, may be used in the above-identified compositions for the denture base and the artificial tooth. It is to be understood that the term "bisphenol-A" is commonly used in the art to indicate chemical compound 2,2-bis(4-hydroxyphenyl)propane.

One of most popular crosslinking dental dimethacrylates is 'bis-GMA' developed by R. L. Bowen about 40 years ago. It is also to be understood that the term "bis-GMA" is commonly used to indicate chemical compound 2,2-bis(4-(2-hydroxy-3-methacryloxypropoxy)-phenyl)propane, otherwise, referred to as "digycidyl methacrylate ester of bis-phenol-A" or "bisphenol-A digycidyl ether" in the dental field.

Bis-GMA type dimethacrylate is superior to other dimethacrylates because of its relatively high molecular weight and stiffness, partially aromatic molecular structure, low polymerization shrinkage, rapid hardening, low volatility, high refractive index, good adhesion property, and excellent mechanical properties of cured resins. Examples of bisphenol A dimethacrylate include ethoxylated bisphenol A dimethacrylate having ethoxy groups (2 moles to 10 moles) and hydrogenated bisphenol A dimethacrylate.

In one example embodiment of the present invention, the total amount of bisphenol A dimethacrylate in the composition for artificial teeth is about 50 to about 75 weight %, preferably about 55 to about 65 weight % based on the total weight of the composition. In another example embodiment of the present invention, the composition for denture base includes about 40 to about 60 weight %, preferably about 45 to about 55 weight % based on the total weight of the composition.

Compounds, such as bisphenol A dimethacrylate, are known and are commercially available. For example, Sartomer company provides such compounds under product names SR348, SR540, SR542, SR480, and SR541. Other companies such as Rahn provide such compounds under the trade names Miramer and Genomer and Cognis also provides such compounds under the trade name Photomer.

In one example embodiment of the present invention, any type of monomeric methacrylates having a functionality of two or more can be employed as component (b) in the composition for artificial tooth. The polyfunctional monomer serves to enhance the curing rate, adjust viscosity, and improve toughness and adhesion between the artificial teeth and the denture base.

Examples of the multifunctional monomeric methacrylates include ethylene glycol dimethacrylate, diethylene glycol dimethacrylate, triethylene glycol dimethacrylate, polyethylene glycol dimethacrylate, 2,2 bis[4-(methacryloxy ethoxy)phenyl]propane, tricyclodecane dimethanol dimethacrylate, 1,10-decanediol dimethacrylate, 1,6-hexanediol dimethacrylate, 1,9-nonanediol dimethacrylate, neopentyl glycol dimethacrylate, 2-hydroxy 1-3 dimethacryloxy propane, trimethylolpropane trimethacrylate, ethoxylated trimethylol propane trimethacrylate, ditrimethyolpropane tetramethacrylate, tris (2-hydroxy ethyl)isocyanurate trimethacrylate, dipentaerythritol pentamethacrylate, ethoxylated pentaerythritol tetramethacrylate, propoxylated glyceryl trimethacrylate, propoxylated trimethylolpropane trimethacrylate, and polyester dendrimer. These compounds are known and commercially available.

For example, Sartomer company provides such compounds under product names SR350, SR262, SR239, SR350, CD401, and SR231. Other companies such as Rahn provide the compounds under the trade names Miramer and Genomer and Cognis also provides such compounds under the trade name Photomer.

For example, the multifunctional monomeric methacrylate in the composition for artificial teeth may be present in about 5 to about 15 weight %, preferably about 7 to about 12 weight % based on the total weight of the liquid photo-curable composition. The multifunctional methacrylate in the composition for denture base may be present in about 5 to about 20 weight %, preferably about 7 to about 15 weight % based on the total weight of the liquid photo-curable composition.

In another example embodiment of the present invention, the combination of the multifunctional monomeric methacrylate can be used and the total amount of the multifunctional monomeric methacrylate is about 5 to about 15 weight %, preferably about 7 to about 12 weight % based on the total weight of the liquid photo-curable composition for artificial teeth and about 5 to about 20 weight %, preferably about 7 to about 15 weight % based on the total weight of the liquid photo-curable composition for denture base.

In one example embodiment of the present invention, urethane methacrylate may be prepared in a known manner as component (c) identified above, for example, by reacting diisocyanate with polyester or polyether polyol to yield isocyanate terminated urethane followed by reacting with hydroxyl terminated methacrylates. This acrylation provides unsaturation or (C=C) groups of the oligomer.

Functionality of such methacrylates should be greater than 2 to be suitable for building a three-dimensional article. The urethane methacrylate may further include aliphatic or aromatic urethane methacrylates and the aliphatic or aromatic chain can be linked by ether or ester groups or a combination thereof.

Urethane methacrylates are also available commercially under the trade name Photomer from Cognis, Genomer 4205, Genomer 4256, and Genomer 4297 from Rahn, Doublemer from Double Bond Chemical Inc., and CN 1963 from Sartomer Company.

In the inventive compositions, the urethane methacrylates having functionality that is greater than 2 and glass transition temperature that is higher than 30° C. may be present in about 15 to about 35 weight %, preferably about 20 to about 30 weight % based on the total weight of the liquid photo-curable composition for artificial teeth. For a composition for denture base, the urethane methacrylates may be present in about 20 to about 45 weight %, preferably about 25 to about 35 weight % based on the total weight of the liquid photo-curable composition.

In another example embodiment of the present invention, a combination of the urethane methacrylates with different functionality or same functionality may be used for the composition for artificial teeth and the composition for denture base. The liquid photo-curable composition for artificial teeth and the liquid photo-curable composition for denture base may further contain a photo-initiator that can be generated as either free-radicals or cations when exposed to UV/Vis light in addition to the unsaturated compound.

Illustrative examples of free-radical photo-initiators include, but are not limited to, acetophenone, anisoin, anthraquinone, (benzene)tricarbonylchromium, benzil, benzoin, benzoin ethyl ether, benzoin isobutyl either, benzoin methyl ether, benzophenone, 3,3',4,4'-benzophenonetetracarboxylic dianhydride, 4-benzoylbiphenyl, 2-benzyl-2-(dimethylamino)-4'-morpholinobutyrophenone, 4,4'-bis(diethylamino)benzophenone, 4,4'-bis(dimethylamino) benzophenone, camphorquinone, 2-chlorothioxanthen-9-one, (cumene)cyclopentadienyliron(II) hexafluorophosphate, dibenzosuberenone, 2,2-diethoxyacetophenone, 4,4'-dihydroxybenzophenone, 2,2-dimethoxy-2-phenylacetophenone, 4-(dimethylamino) benzophenone, 4,4'-dimethylbenzyl, 2,5-dimethylbenzophenone, 3,4-dimethylbenzophenone, 4'-ethoxyacetophenone, 2-ethylanthraquinone, ferrocene, 3'-hydroxyacetophenone, 4'-hydroxyacetophenone, 3-hydroxybenzophenone, 4-hydroxybenzophenone, 1-hydroxycyclohexyl phenyl ketone, 2-hydroxy-2-methylpropiophenone, 2-methylbenzophenone, 3-methylbenzophenone, methylbenzoylformate, 2-methyl-4'-(methylthio)-2-morpholinopropio-phenone, phenanthrenequinone, 4'-phenoxyacetophenone, thioxanthen-9-one, triacrylsulfonium hexafluoroantimonate salts, and triarylsulfonium hexafluorophosphate salts.

Among the previously identified free-radical photo-initiators, the acylphosphine oxide compounds provide excellent polymerizability in UV/Vis light and have been recently used in the dental field. The composition using a visible light photo-initiator composed of the acylphosphine oxide compound showed an excellent curability of a thin-layer surface, which is an important property for the three-dimensional printing. Therefore, a visible light photo-initiator used for artificial teeth and denture base may be (bis)acylphosphine oxides or preferably camphorquinone.

Among (bis)acylphosphine oxides used as a photo-initiator, examples of the acylphosphine oxides include 2,4,6-trimethylbenzoyldiphenylphosphine oxide, 2,6-dimethyoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, and benzoyl di-(2,6-dimethylphenyl)phosphonate. Examples of the bisacylphosphine oxides include bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-prophylphenylphosphine oxide, bis-(2,6-dichlorobenzoyl)-1-naphthylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide, and (2,5,6-trimethylbenzoyl)-2,4,4-trimethylpentylphosphine oxide.

The cationic photo-initiators may be onium salts. The cationic species of the photo-initiator may be, for example, iodonium, sulfonium, oxoisothiochromanium, or similar compounds. These compounds are known and commercially available.

For example, Dow Chemical Company provides such compounds under product names UVI 6950, UVI 6970, UVI 6974, UVI 6976, and UVI 6990. Such compounds are also provided by other companies such as Ciba company under the trade name Irgacure and Double Bond Chemical Inc. the under trade name DoubleCure. Combinations including more than one of the foregoing photo-initiators may be used in the inventive compounds.

Each of the free radical photo-initiator and the cationic photo-initiator is individually utilized in the artificial teeth and denture base compositions to initiate polymerization under the UV/Vis light. The photo-initiators may be utilized in an amount from about 0.01 to about 10 weight %, preferably from about 0.1 to about 5 weight %, more preferably about 0.15 to about 3 weight %, based on the total weight of the composition.

According to example embodiments of the present invention, the composition may contain inorganic fillers. Examples of inorganic filler material include fused silica, synthetic silica, alumina silicate, amorphous silica, glass ceramic, soda glass, lithium borosilicate glass, barium glass, strontium glass, zinc glass, fluoroaluminum borosilicate glass, borosilicate glass, crystal quartz, and a mixture thereof. The inorganic filler particle may include silica particles having an average diameter of less than about 300 nm, preferably less than about 200 nm. The silica particles used in the composition according to example embodiments of the present invention are preferably substantially spherical and substantially non-porous.

Moreover, the inorganic filler including silica-based fine particles and coatings of an oxide that cover the surfaces of the silica-based fine-particles may be used in the composition. The oxide may contain a zirconium atom, a silicon atom, and an oxygen atom to provide excellent transparency.

Suitable nano-sized silicas are commercially available from DeGussa AG, (Hanau, Germany) under product name Aerosil OX-50, -130, -150, and -200 or from Cabot Corp (Tuscola, Ill.) under product name Cab-o-sil M5.

In the filler, the oxide coating layers of fine particles may be functionalized using reactive components and this functionalization of the fine particles is called surface-modification or surface-treatment. The surface-modification or surface-treatment provides reactivity to fillers that participate in a chemical reaction and/or homogenous dispersion in a compounding system. Surface-modified nano-sized silica particles provide stable dispersion in the solution before the composition is used since the particles do not aggregate and are not settled after standing for a certain period of time at room temperature. The surface-modified particles are well dispersed in the photo-curable composition, and thus, help achieving a substantially homogenous composition.

The surface-modified silica particles according to an example embodiment of the present invention are preferably treated with a resin-compatibilizing surface treatment agent. For example, preferred surface treatment or surface modifying agents include silane treatment agents.

When a surface of silica particle is modified or coated with silane treatment agents having functional groups such as acryl group or methacryl group that can participate in the polymerization reaction in a methacrylate composition, the silica particle is referred to as functionalized silane-treated particles. If the surface of silica particle is not modified or coated, the silica particle is referred to as unfunctionalized silane-treated silica.

Examples of the surface modifying silane agents include methyltrimethoxysilane, dimethyldimethoxysilane, phenyltrimethoxysilane, diphenyldimethoxysilane, methyltriethoxysilane, dimethyldiethoxysilane, vinyltrimethoxysilane, vinyltriethoxysilane, methyldichlolorsilane, dimethyldichlorosilane, trimethylchlorosilane, vinyltrichlorosilane, trimethylbromosilane, diethylsilane, and similar agents.

Among these, a surface modifying agent having functional group which can be reacted in the polymerization during curing may include, for example, ω-methacryloxyalkyl trimethoxysilane having 3 to 15 carbon atoms between a methacryloxy group and a silicon atom, ω-methacryloxyalkyl triethoxysilane having 3 to 15 carbon atoms between a methacryloxy group and a silicon atom, vinyltrimethoxysilane, vinyltriethoxysilane, vinyltriacetoxysilane, and γ-glycidoxypropyltrimethoxysilane. More preferable silane treatment agent includes 3-methacryloxypropyltrimethoxysilane, 8-methacryloyloxyoctyltrimethoxysilane, 9-methacryloyloxynonyltrimethoxysilane, 10-methacryloyloxydecyltrimethoxysilane, 11-methacryloyloxyundecyltrimethoxysilane, 11-methacryloyloxyundecyldichloromethylsilane, and 11-methacryloyloxyundecyltrichlorosilane.

These surface modifying agents may be used alone, or as a combination of two or more thereof. These agents are available commercially under the trade name Genosil GF31 and XL33 and in particular, 3-glycidoxypropyltrimethoxy silane is available commercially under the trade name Genosil GF80 and GF82 from Wacker Chemie AG and Aerosil R7200 from Evonik.

In another example embodiment of the present invention, the compositions may include, but are not limited to, a heavy metal oxide. For example, a suitable metal oxide may be an oxide of metals having an atomic number that is greater than 30 such as tungsten, bismuth, molybdenum, tin, zinc, cerium, yttrium, strontium, barium, zirconium, hafnium, niobium, tantalum, and a combination thereof.

The heavy metal oxide particles preferably have an average diameter of less than about 100 nm, more preferably less than about 70 nm, most preferably less than about 60 nm. Sometimes the heavy metal oxide can be aggregated and the aggregated particles should be less than about 200 nm, preferably less than about 100 nm in average diameter.

In another example embodiment of the present invention, the amount of the surface-treated silica fine particles may be from about 1% to about 45%, preferably from about 10% to about 35% based on the total weight of the composition for artificial tooth and from about 0% to about 25%, preferably from about 0% to about 15% based on the total weight of the composition for denture base.

In one example embodiment of the present invention, the mixture optionally may include a pigment composition including a pigment or combination of pigments to provide a desired color. Various combinations of pigments and dyes may be used. In another example embodiment, the amount of the combination of pigments may be less than about 0.5 weight %, preferably less than about 0.25 weight % based on the total weight of the composition.

The pigments should be sized to be injectable from the nozzle of the print head without severely clogging the nozzle, capillaries, or other parts of the printing equipment. The viscosity of the composition with pigments may be affected by the size of the pigments. A preferred size of the pigment is from about 0.1 to about 600 nm, more preferably from about 10 to about 200 nm.

The color of the pigments is not limited to a particular color. Possible colors of the pigments include, for example, white, yellow, orange, black, green, red, violet, and like.

In one example embodiment of the present invention, the composition may optionally include a surface tension reducing agent to provide lower surface tension by lowering surface energy, better wettability, and a small drop size to the formulation in order to minimize the satellite drops tail during the jetting or printing process. Examples of the surface tension reducing agent include silicone surface additives, marketed by Byk Chemie under the trade name Byk or marketed by Dow Corning under the trade name Dow Corning series.

In one example embodiment of the present invention, the composition may also include one or more stabilizers. Suitable stabilizers include, but are not limited to, 4-methoxyphenol, butylated hydroxytoluene (2,6-di-t-butyl-4-methylphenol), phenothiazine, bistridecylthiodipropionate, and hinder amines.

In recent years, a large number of three-dimensional printing technologies have been introduced and are available to produce three-dimensional objects. For example, three-dimensional printing technologies include selective laser sintering (SLS), fused deposition molding (FDM), laminate object manufacturing (LOM), rapid prototyping, and three-dimensional inkjet printing. These three-dimensional printing technologies find use in a variety of fields, for example, jewelry, footwear, architecture, engineering and construction, automotive, aerospace, dental and medical industries, education, geographic information systems, civil engineering, and many others.

Among these technologies, three-dimensional printing methods using digital light processing (DLP) or an injection through a series of tiny nozzles or a single nozzle may use photo-curable materials in a wax or liquid state which can be cured by UV/Vis light. These two methods are most effectively optimized for speed, low cost, high resolution, and ease-of-use, making them suitable for visualizing during conceptual stages of engineering design and early-stage functional testing.

Generally, complicated three-dimensional articles in an ink-jet printing method that can load several different materials are produced from photo-curable liquid compositions by jetting followed by exposure to UV/Vis light. The photo-curable ink in the ink-jet printing process is jetted through several nozzles on the building platform with a pattern defined by a computer aided design (CAD) file.

Once the photo-curable liquid is placed on top of the solid layer, such as a support layer or building layer, it turns from liquid to solid following exposure to UV/Vis light due to polymerization of the liquid. In order to introduce fresh liquid of a required quantity to provide a specified thickness of a surface layer of the photo curable liquid that will be formed as a photo-cured layer on the previously superposed photo-cured layer, the printing head or the product being printed should move precisely by a distance that is equal to the specified thickness during the procedure.

This procedure is repeated until desired three-dimensional articles are obtained. After the desired three-dimensional articles are obtained, the support layers are optionally washed out with either water or solvent if the system requires the support materials in order to accurately form the three-dimensional articles. Since an inkjet type printer can load several materials depending on the option, artificial teeth and denture base can printed as a single body.

In a three-dimensional printing method using digital light processing, the photo-curable liquid is placed in a vat or container. The material is defined by the exposed area that is cured by the digital light processing. Once a layer has been cured by UV/Vis light, a building platform moves in the z-direction depending on the thickness of the layer.

This process is repeated until all layers are formed. According to this printing method, since only one material is loaded, the artificial teeth and denture base are printed separately and then the printed artificial tooth or teeth and denture base are combined together to form denture.

The process for making a set of artificial teeth and denture base preferably uses an inkjet type or digital light process printing method. For example, the Connex, Eden and Desktop families supplied by Objet or Master supplied by Carima and The Form 1 supplied by Formlabs provide such a printing method.

The composition used in the inkjet system or digital light processing system for three-dimensional articles is subjected to several restrictions. For example, for such compositions, its viscosity should not be more than about 1000 cps at the time and temperature of jetting or spreading but the produced articles should be accurate and have good mechanical properties.

As described above, in case of the inkjet system for three-dimensional articles, the viscosity of the ink composition is required to be less than about 500 cps at the temperature when the application thereof is carried out. However, if the viscosity is greater than 500 cps at the time of jetting, this condition will be fulfilled by heating the ink composition at the time of jetting from the nozzle.

Although the photo-curable composition for an inkjet system to produce three-dimensional articles should have low viscosity at the time of jetting such that it can be injected by the ink jet system, it allows formation of a patterned layer by immediate light curing to have physical properties required for a workable three-dimensional article or part, such as tensile strength, flexural modulus, and hardness.

Since the photo-curable liquid superposes the solid layers having a specified thickness on top of another layer to form a three-dimensional article, the freshly displaced liquid layer is cured quickly following exposure to UV/Vis light such that the formed solid layer becomes ready for another layer of new liquid material. This means that the photo-curable liquid composition for three-dimensional articles requires fast curing, fast setting, proper shrinkage, and good mechanical properties.

Most light-curable compositions including ink formulations, as disclosed in the above-identified patent documents, are not suitable for production of complicated three-dimensional articles with smooth and accurate dimension by an inkjet printing method. This is because the resin mixtures disclosed in these patent documents would be either too viscous or not sufficiently viscous, too light sensitive or not sufficiently light sensitive, slowly cured, and subject to excessive shrinkage such that mechanical properties required for functional three-dimensional articles are not achieved.

Under these limitations, the viscosity of the composition for artificial teeth and denture base according to an example embodiment of the present invention is controlled to be between less than about 500 cps at the jetting or spreading temperature that is in the range of about 60° C. to about 80° C.

In exemplary embodiments of the present invention, the viscosity of the composition is measured using a Brookfield DV II+ Programmable Viscometer equipped with a proper spindle at 50 rpm and at two different temperatures, i.e., room temperature and 70° C. Before measuring the viscosity, the composition is held for 3 hours in an oven which was set as to be at 70° C. In an oven or autoclave having an intense visible light source, a set of printed artificial teeth and denture base combined using dental adhesives are annealed at around 30° C.-160° C. for at least 2 hours to 5 days to improve the mechanical properties of the denture and adhesion between the printed artificial teeth and denture base.

Example

Each of the light polymerizable resin mixtures for manufacturing of three-dimensional articles by a digital light process method was prepared by mixing relevant components shown in Tale 1 for denture base and Table 2 for artificial teeth for several hours to obtain a dispersal system, and then filtering the mixed components through a filter of 50 µm. The test specimen was prepared using a three-dimensional printer. Table 1 for denture base and Table 2 for artificial teeth include their physical properties.

TABLE 1

| | Denture base | | |
|---|---|---|---|
| | Example 1 | Example 2 | Example 3 |
| Composition | | | |
| Ethoxylated bisphenol A dimethacrylate | 40-50% | 45-55% | 55-60% |
| Urethane dimethacrylate | 40-45% | 35-40% | 20-25% |
| Trimethylolpropane trimethacrylate | 5-10% | 5-10% | 5-15% |
| Methacrylsilane treated silica | 0% | 3-6% | 5-10% |
| Bis acylphosphine oxide | 0.5-3% | 1-5% | 1-5% |
| Composition Properties | | | |
| Viscosity at 25° C. (cps) | 2800 | 2900 | 2750 |
| Viscosity at 70° C. (cps) | 120 | 160 | 200 |
| Exposure time (seconds) | 6 | 7 | 8 |
| Flexural modulus (Mpa) | 2100 | 2300 | 2900 |
| Flexural strength (Mpa) | >65 | >65 | >65 |
| Translucency | Good | Good | Good |
| Porosity | No | No | No |

TABLE 2

| | Artificial tooth | | |
|---|---|---|---|
| | Example 1 | Example 2 | Example 3 |
| Composition | | | |
| Ethoxylated bisphenol A dimethacrylate | 55-70% | 55-70% | 50-60% |
| Urethane dimethacrylate | 20-35% | 15-25% | 20-30% |
| Trimethylolpropane trimethacrylate | 5-15% | 5-15% | 5-15% |
| Methacrylsilane treated silica | 8-13% | 13-17% | 20-35% |
| Bis acylphosphine oxide | 0.5-3% | 1-5% | 1-5% |
| Composition Properties | | | |
| Viscosity at 25° C. (cps) | 2750 | 4200 | 5000 |
| Viscosity at 70° C. (cps) | 200 | 350 | 400 |
| Exposure time (seconds) | 8 | 8 | 9 |
| Flexural modulus (Mpa) | 2900 | 2800 | 3100 |
| Vickers Hardness | 20 | 22 | 23 |

Test specimens of examples 1, 2, and 3 shown in Tables 1 and 2 for flexural strength and flexural modulus tests were printed and measured by using a three-point bend test on Instron bending unit according to ASTM D790 after post curing.

Exposure time in Table 1 is a length of time to cure and solidify each layer before stacking a new layer on top of the cured layer. The curing light used was visible light in the range of about 370 to about 700 nm wavelengths. Post curing was carried out at 45° C. for a period of 5 days, using a UV/Vis curing equipment available from Honle UV Technology.

Using a three-dimensional printer by a digital light processing method, the denture base and artificial teeth were separately printed and then the printed denture base and artificial teeth were assembled together using dental adhesives. The denture shown in FIG. 3 can be formed using a three-dimensional printer by an inkjet printing method that can jet three different materials simultaneously without printing artificial teeth and denture base individually, and thus, no adhesion process is required in this method.

Figure 2:
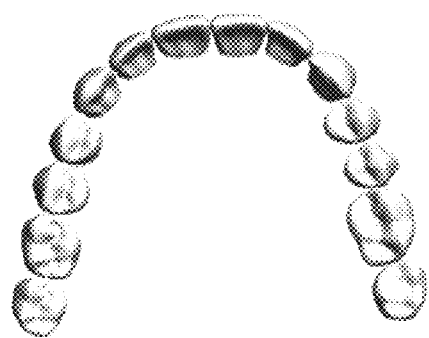
FIG. 2 is a schematic view of an array of artificial teeth to be formed by three-dimensional printing and to be placed on a denture base according to an exemplary embodiment of the present invention.
Figure 2:
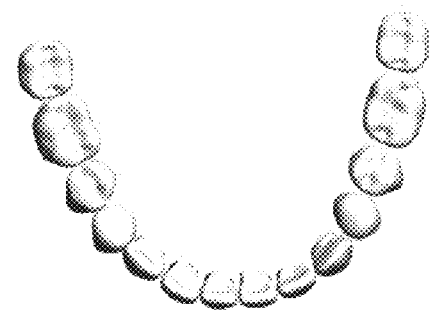
Figure 2:
Figure 2:
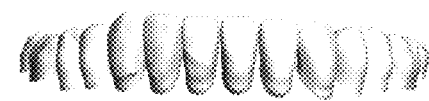
Figure 3:
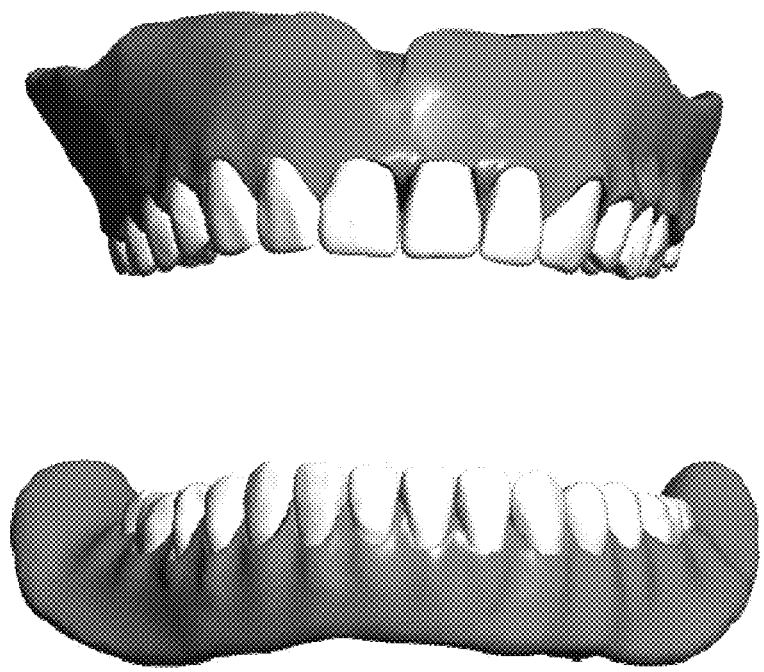
FIG. 3 is a schematic view of denture formed by integration of the artificial teeth and the denture base that are made of a photo-curable composition according to an exemplary embodiment of the present invention.

FIG. 1 shows the top and front views of a denture base having a resting area for artificial teeth sets after printing using a three-dimensional printer. FIG. 2 shows the top and front views of a set of artificial teeth after printing using a three-dimensional printer that are put into the resting area of the denture base. FIG. 3 shows a denture formed after adhesion between the artificial teeth and the denture base. The same denture as shown in FIG. 3 will be achieved with a three-dimensional printer by an inkjet printing method. Some of artificial teeth can be printed individually and assembled together to the denture base, using dental adhesives, to generate full or partial denture.

To observe distribution of the surface modified silica fine particles in the organic matrix, pictures of the cross-sectional area of the sample specimen were taken with a high performance scanning electron microscope (SEM) under acceleration voltage of 20 KV, and 400 magnification. The picture (not shown) revealed evenly dispersed silica particles in the cured matrix and no porosity was observed. Vickers hardness test was performed at room temperature according to ASTM E384 after the post curing at 45° C. for 5 days, using a hardness tester DUH-211 (Dong-il Shimadzu corp.).

It will be apparent to those skilled in the art that various modifications and variations can be made in the example embodiments of the present invention without departing from the spirit or scope of the invention. Thus, it is intended that the present invention covers the modifications and variations of the example embodiments disclosed herein provided they come within the scope of the appended claims and their equivalents.

What is claimed is:

1. A composition comprising:
   about 50 to about 75 weight % of at least one kind of ethoxylated difunctional bisphenol A dimethacrylate;
   about 5 to about 15 weight % of at least one kind of multifunctional methacrylate having two or more methacryloxy groups;
   about 15 to about 35 weight % of at least one kind of urethane dimethacrylate;
   about 5 to about 35 weight % of at least one kind of silica-based fine particles having methacrylate functionalization layers and having an average particle size of less than about 200 nm;
   about 0.2 to about 5.0 weight % of at least one kind of ultraviolet/visible (UV/Vis) light-photo-polymerization initiator;
   at least one colorant; and
   at least one stabilizer,
   wherein viscosity of a liquid state mixture, including the at least one kind of ethoxylated difunctional bisphenol A dimethacrylate, the at least one kind of multifunctional methacrylate, the at least one kind of urethane dimethacrylate, the at least one kind of silica-based fine particles, the at least one kind of UV/Vis light-photo-polymerization initiator, the at least one colorant, and the at least one stabilizer, is from 2000-5200 centipoise (cps) at room temperature and from 50 to 500 cps at 70° C., and
   wherein the viscosity is adjusted by controlling a ratio of the at least one kind of ethoxylated difunctional bisphenol A dimethacrylate, the at least one kind of multifunctional methacrylate, the at least one kind of urethane dimethacrylate, the at least one kind of silica-based fine particles, the at least one kind of UV/Vis light-photo-polymerization initiator, the at least one colorant, and the at least one stabilizer in the mixture.

2. A composition comprising:
   about 40 to about 60 weight % of at least one kind of ethoxylated difunctional bisphenol A dimethacrylate;
   about 5 to about 20 weight % of at least one kind of multifunctional methacrylate;
   about 20 to about 45 weight % of at least one kind of urethane dimethacrylate;
   about 0 to about 15 weight % of at least one kind of silica-based fine particles having methacrylate functionalization layers and having an average particle size of less than about 200 nm;
   about 0.2 to about 5.0 weight % of at least one kind of ultraviolet/visible (UV/Vis) light-photo-polymerization initiator;
   at least one colorant; and
   at least one stabilizer,
   wherein viscosity of a liquid state mixture, including the at least one kind of ethoxylated difunctional bisphenol A dimethacrylate, the at least one kind of multifunctional methacrylate, the at least one kind of urethane dimethacrylate, the at least one kind of silica-based fine particles, the at least one kind of UV/Vis light-photo-polymerization initiator, the at least one colorant, and the at least one stabilizer, is from 2000-5200 centipoise (cps) at room temperature and from 50 to 500 cps at 70° C., and
   wherein the viscosity is adjusted by controlling a ratio of the at least one kind of ethoxylated difunctional bisphenol A dimethacrylate, the at least one kind of multifunctional methacrylate, the at least one kind of urethane dimethacrylate, the at least one kind of silica-based fine particles, the at least one kind of UV/Vis light-photo-polymerization initiator, the at least one colorant, and the at least one stabilizer in the mixture.

3. The composition of claim 1, wherein the light-photo-polymerization initiator comprises acylphosphine oxide compounds.

4. The composition of claim 1, wherein the silica-based fine particles comprise reactive silica particles that are surface-modified by a surface modifying agent.

5. The composition of claim 4, wherein the surface modifying agent comprises compounds containing methacryloxy groups.

6. A method of printing a denture using the composition of claim 1, the method comprising:
   stacking layers of the mixture and curing the stacked layers one-by-one using a three-dimensional printer based on Computer-Aided Design/Computer-Aided Manufacturing (CAD/CAM) generated information that is related to the denture to be manufactured.

7. The method of claim 6, wherein the three-dimensional printer is operated according to an ink-jet printing method or a digital light processing method.

8. The method of claim 6, wherein the information comprises a digital model generated based on a dental impression of a patent's mouth and a CAD/CAM design.

9. The method of claim 6, further comprising performing post-treatment to the printed denture to improve surface quality of the denture.

10. The method of claim 6, further comprising performing a post-curing operation on the printed denture at about 30 to about 160° C.

11. The method of claim 6, wherein the denture comprises a printed denture base portion and a printed artificial tooth portion formed as a single body.

12. The method of claim 6, further comprising assembling a denture base and artificial teeth with dental adhesives after using the three-dimensional printer to separately print the denture base and the artificial teeth.

13. The method of claim 6, wherein the denture comprises a partial denture and a full denture.

14. A method for manufacturing a denture using a three-dimensional printer and light-curable materials based on denture information, the method comprising:
   manufacturing a denture base from a first composition; and
   manufacturing at least one artificial tooth from a second composition that is different from the first composition,
   wherein:
   the first composition comprises:
      about 40 to about 60 weight % of at least one kind of ethoxylated difunctional bisphenol A dimethacrylate;
      about 5 to about 20 weight % of at least one kind of multifunctional methacrylate;
      about 20 to about 45 weight % of at least one kind of urethane dimethacrylate;
      about 0 to about 15 weight % of at least one kind of a silica-based fine particles having methacrylate functionalization layers and having an average particle size of less than about 200 nm;
      about 0.2 to about 5.0 weight % of at least one kind of ultraviolet/visible (UV/Vis) light-photo-polymerization initiator;
      at least one colorant; and
      at least one stabilizer, wherein viscosity of a first liquid state mixture, including the at least one kind of ethoxylated difunctional bisphenol A dimethacrylate, the at least one kind of multifunctional methacrylate, the at least one kind of urethane dimethacrylate, the at least one kind of silica-based fine particles, the at least one kind of UV/Vis light-photo-polymerization initiator, the at least one colorant, and the at least one stabilizer, is from 2000-5200 centipoise (cps) at room temperature and from 50 to 500 cps at 70° C., and wherein the viscosity of the first liquid state mixture is adjusted by controlling a ratio of the at least one kind of ethoxylated difunctional bisphenol A dimethacrylate, the at least one kind of multifunctional methacrylate, the at least one kind of urethane dimethacrylate, the at least one kind of silica-based fine particles, the at least one kind of UV/Vis light-photo-polymerization initiator, the at least one colorant, and the at least one stabilizer in the mixture; and the second composition comprises:
about 50 to about 75 weight % of at least one kind of ethoxylated difunctional bisphenol A dimethacrylate;
about 5 to about 15 weight % of at least one kind of multifunctional methacrylate having two or more methacryloxy groups;
about 15 to about 35 weight % of at least one kind of urethane dimethacrylate;
about 5 to about 35 weight % of at least one kind of a silica-based fine particles having or methacrylate functionalization layers and having an average particle size of less than about 200 nm;
about 0.2 to about 5.0 weight % of at least one kind of ultraviolet/visible (UV/Vis) light-photo-polymerization initiator;
at least one colorant; and
at least one stabilizer, wherein viscosity of a second liquid state mixture, including the at least one kind of ethoxylated difunctional bisphenol A dimethacrylate, the at least one kind of multifunctional methacrylate, the at least one kind of urethane dimethacrylate, the at least one kind of silica-based fine particles, the at least one kind of UV/Vis light-photo-polymerization initiator, the at least one colorant, and the at least one stabilizer, is from 2000-5200 centipoise (cps) at room temperature and from 50 to 500 cps at 70° C., and wherein the viscosity of the second liquid state mixture is adjusted by controlling a ratio of the at least one kind of ethoxylated difunctional bisphenol A dimethacrylate, the at least one kind of multifunctional methacrylate, the at least one kind of urethane dimethacrylate, the at least one kind of silica-based fine particles, the at least one kind of UV/Vis light-photo-polymerization initiator, the at least one colorant, and the at least one stabilizer in the mixture.

* * * * *